(12) United States Patent
Mayeaux

(10) Patent No.: US 7,051,604 B1
(45) Date of Patent: May 30, 2006

(54) HEAT PIPE SAMPLE FLUID PROBE

(75) Inventor: Donald P. Mayeaux, St. Amant, LA (US)

(73) Assignee: Mayeaux Holding LLC, Gonzales, LA (US)

( * ) Notice: Subject to any disclaimer, the term of this patent is extended or adjusted under 35 U.S.C. 154(b) by 0 days.

(21) Appl. No.: 10/743,628

(22) Filed: Dec. 22, 2003

Related U.S. Application Data

(60) Continuation-in-part of application No. 09/915,192, filed on Jul. 25, 2001, now Pat. No. 6,701,794, and a continuation-in-part of application No. 09/162,239, filed on Sep. 28, 1998, now Pat. No. 6,357,304, which is a continuation-in-part of application No. 08/701,406, filed on Aug. 22, 1996, now Pat. No. 5,841,036, application No. 10/743,628, which is a continuation-in-part of application No. 10/408,026, filed on Apr. 3, 2003, now Pat. No. 6,904,816, which is a division of application No. 09/162,239, filed on Sep. 28, 1998, now Pat. No. 6,357,304, which is a continuation-in-part of application No. 08/701,406, filed on Aug. 22, 1996, now Pat. No. 5,841,036.

(60) Provisional application No. 60/221,335, filed on Jul. 26, 2000.

(51) Int. Cl.
*G01N 1/20* (2006.01)
*G01N 1/22* (2006.01)

(52) U.S. Cl. ............................ 73/863.12; 73/863.11; 73/863.23; 73/863.81

(58) Field of Classification Search .............................. 73/863.11–863.21, 863.23, 863.81, 863.85, 73/863.86, 864.73, 864.74
See application file for complete search history.

(56) References Cited

U.S. PATENT DOCUMENTS

| | | | | |
|---|---|---|---|---|
| 4,617,985 A | * | 10/1986 | Triggs et al. | 165/272 |
| 4,671,298 A | * | 6/1987 | Babb et al. | 600/532 |
| 4,702,114 A | * | 10/1987 | Cabannes | 73/863.85 |
| 4,856,352 A | * | 8/1989 | Daum et al. | 73/863.12 X |
| 5,531,130 A | * | 7/1996 | Welker | 73/863.81 |
| 6,481,299 B1 | * | 11/2002 | Silvis et al. | 73/863.81 |

FOREIGN PATENT DOCUMENTS

| | | | | |
|---|---|---|---|---|
| GB | 2162310 A | * | 1/1986 | 73/863.11 |
| JP | 56067732 A | * | 6/1981 | 73/863.11 |
| JP | 57203934 A | * | 12/1982 | 73/863.12 |

* cited by examiner

*Primary Examiner*—Thomas P. Noland
(74) *Attorney, Agent, or Firm*—Joseph T. Regard Ltd plc

(57) ABSTRACT

A system for the collection and initial conditioning of sample gas for "on-line" analyzers, or filling of gas sample cylinders. The preferred embodiment of the present invention contemplates a system configured to obtain a representative gas phase sample from a process gas containing entrained liquid, or a process gas which generally is susceptible to partial condensation of some gas phase components. The preferred embodiment of the present invention teaches a sample probe assembly including a heat pipe configured for maintaining sample gas drawn through said sample probe at or near the source gas temperature and pressure. Accuracy of the analysis of source gas stream is enhanced and compositional changes of the gas phase are avoided by preventing the partial condensation of gas components or vaporization of entrained liquid. Alternative embodiments teach the insulation of the sampling conduit to maintain the sample gas at an isothermal condition equivalent to that of the fluid stream from which it is sampled.

14 Claims, 9 Drawing Sheets

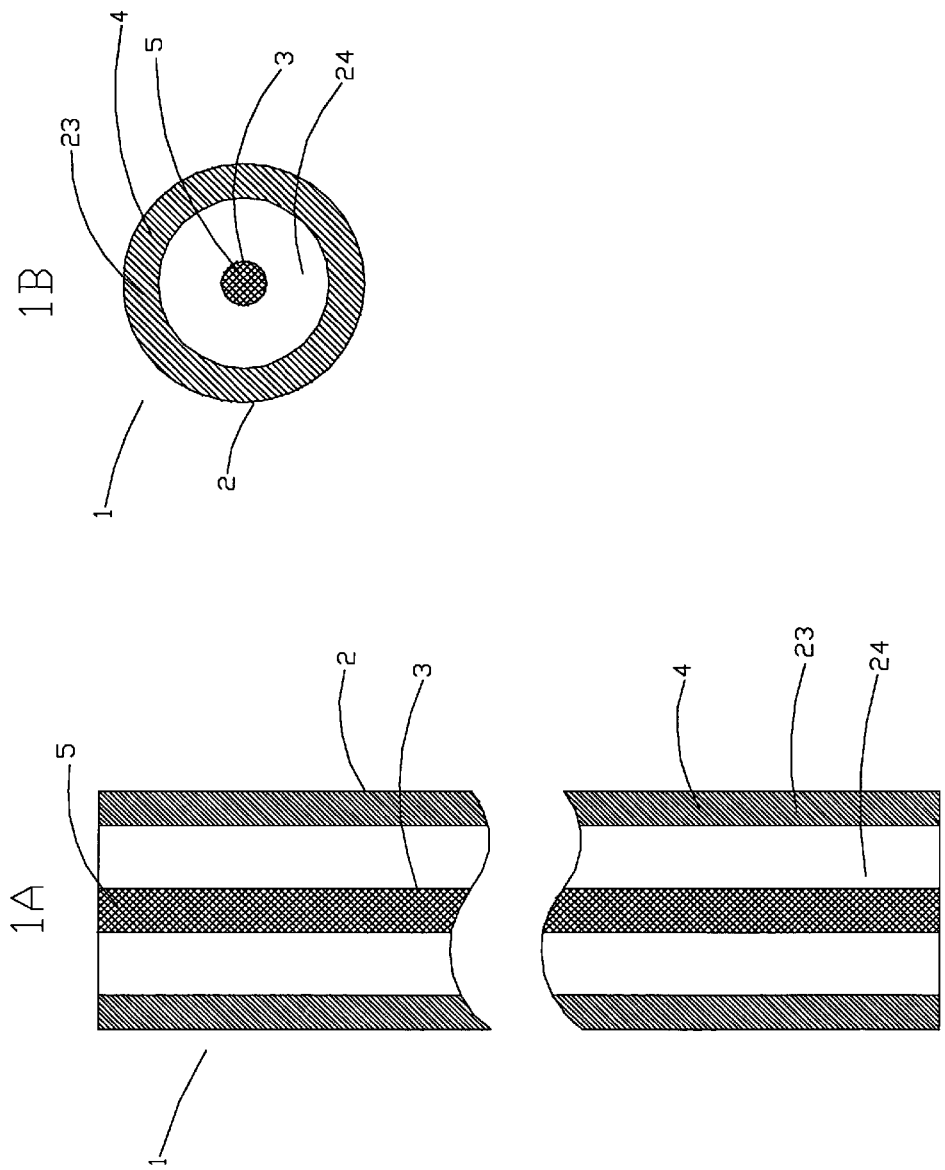

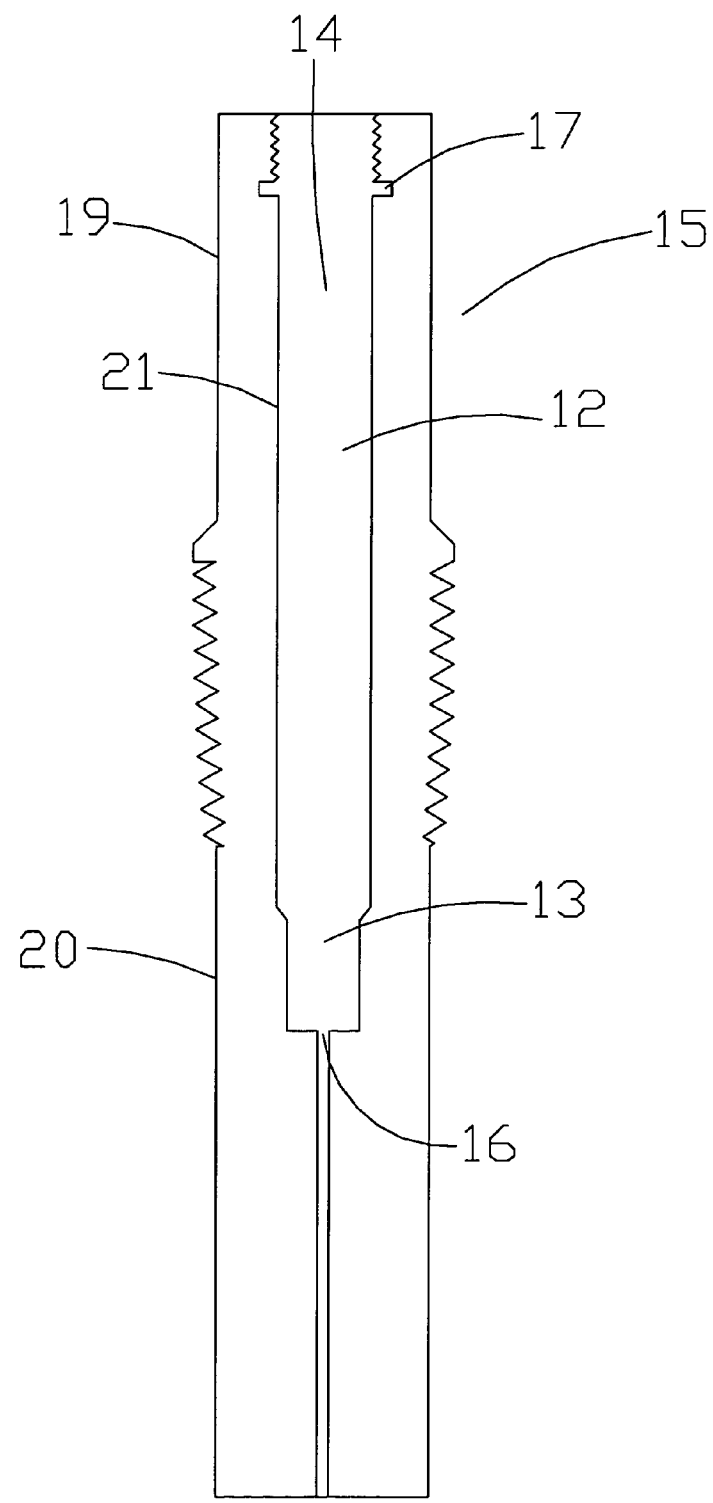
Figure #2

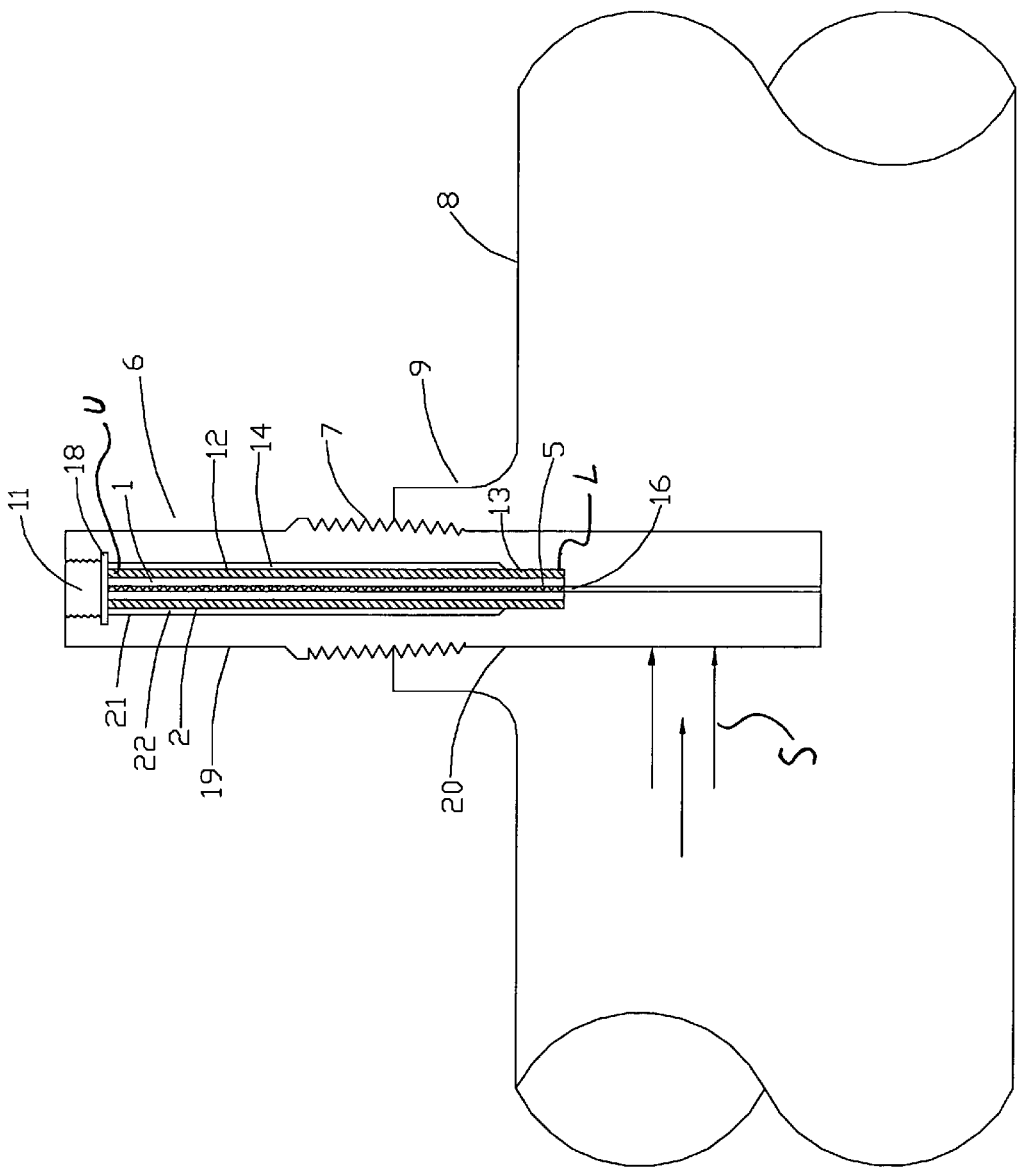

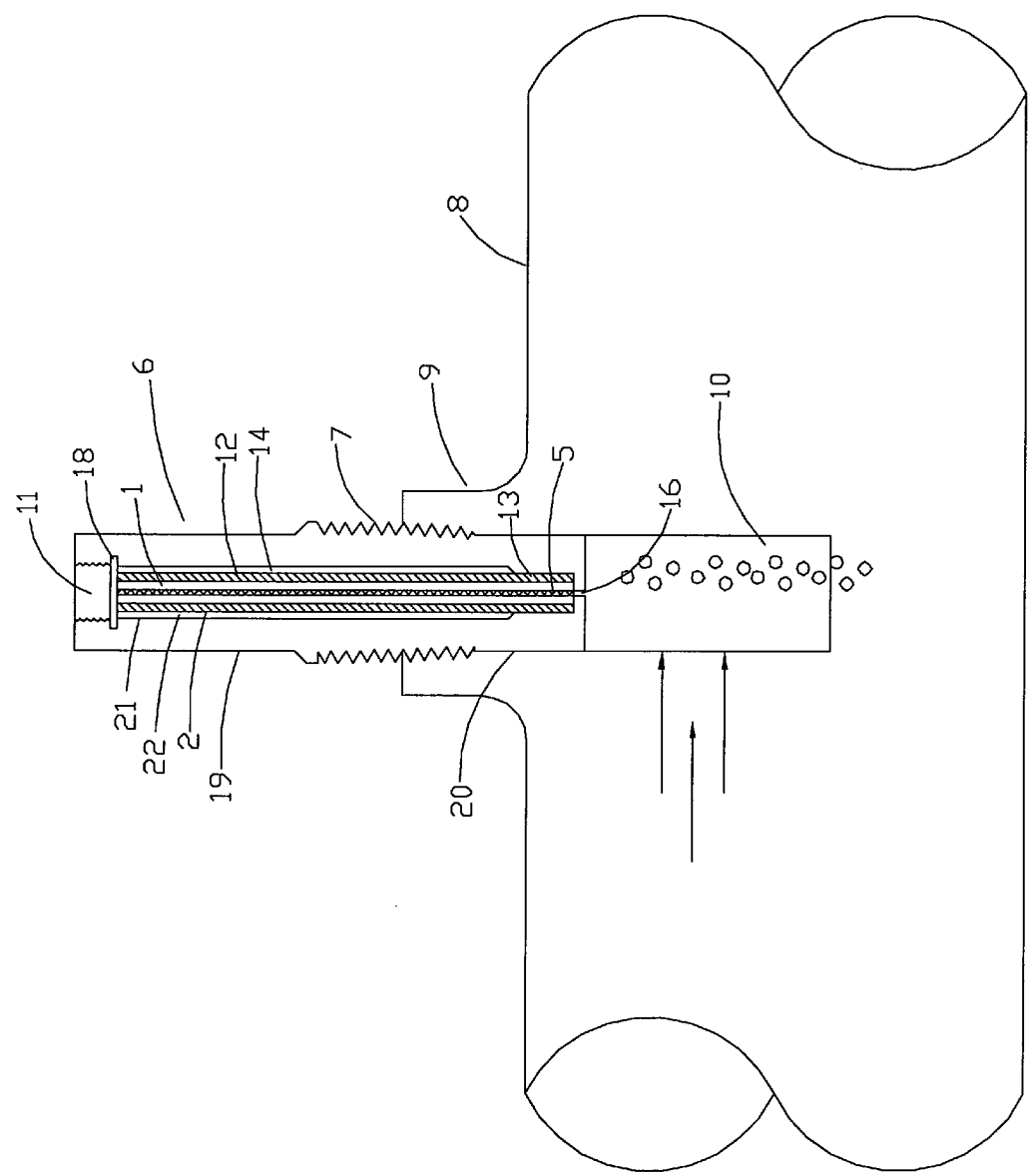
Figure #4

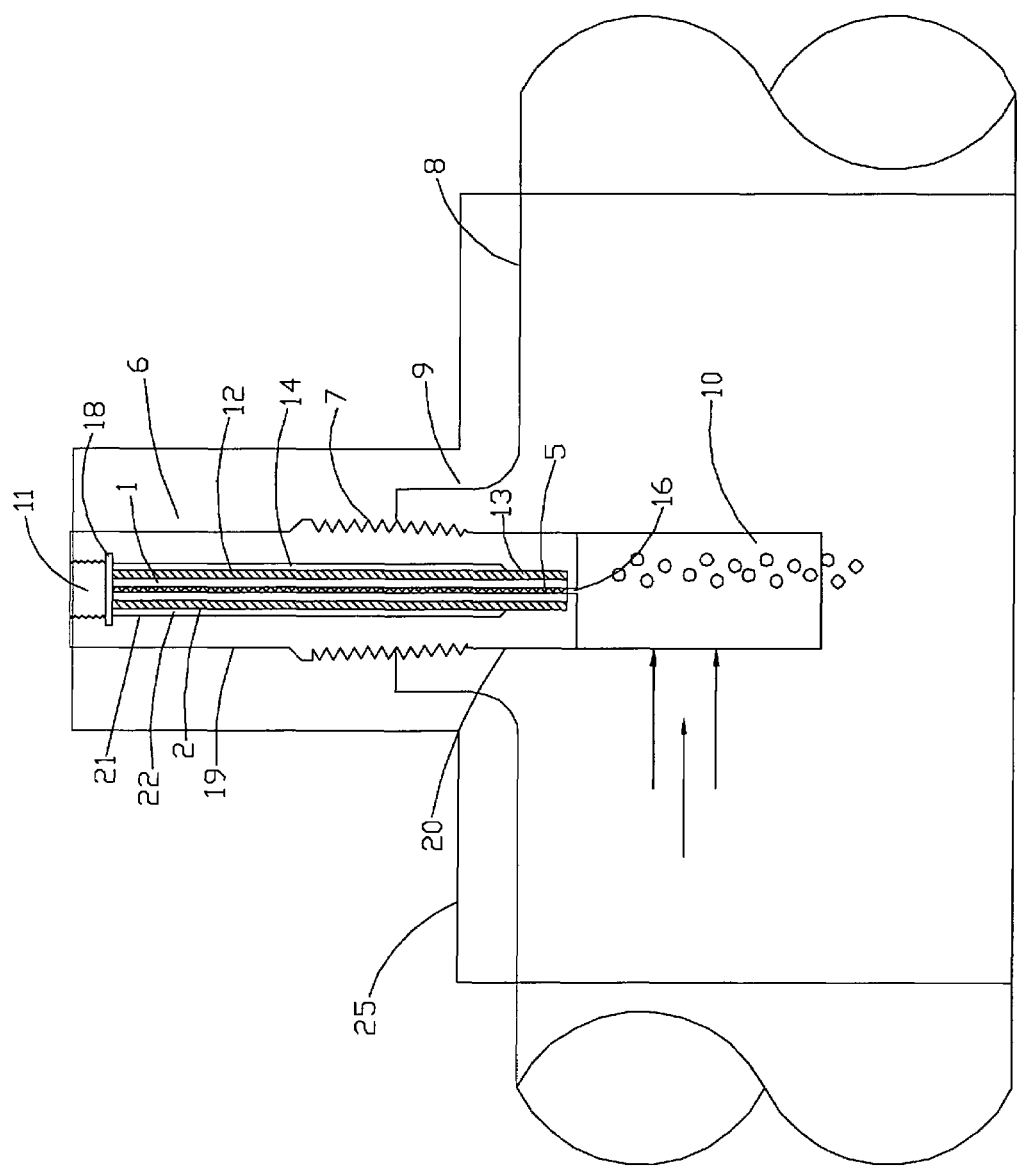

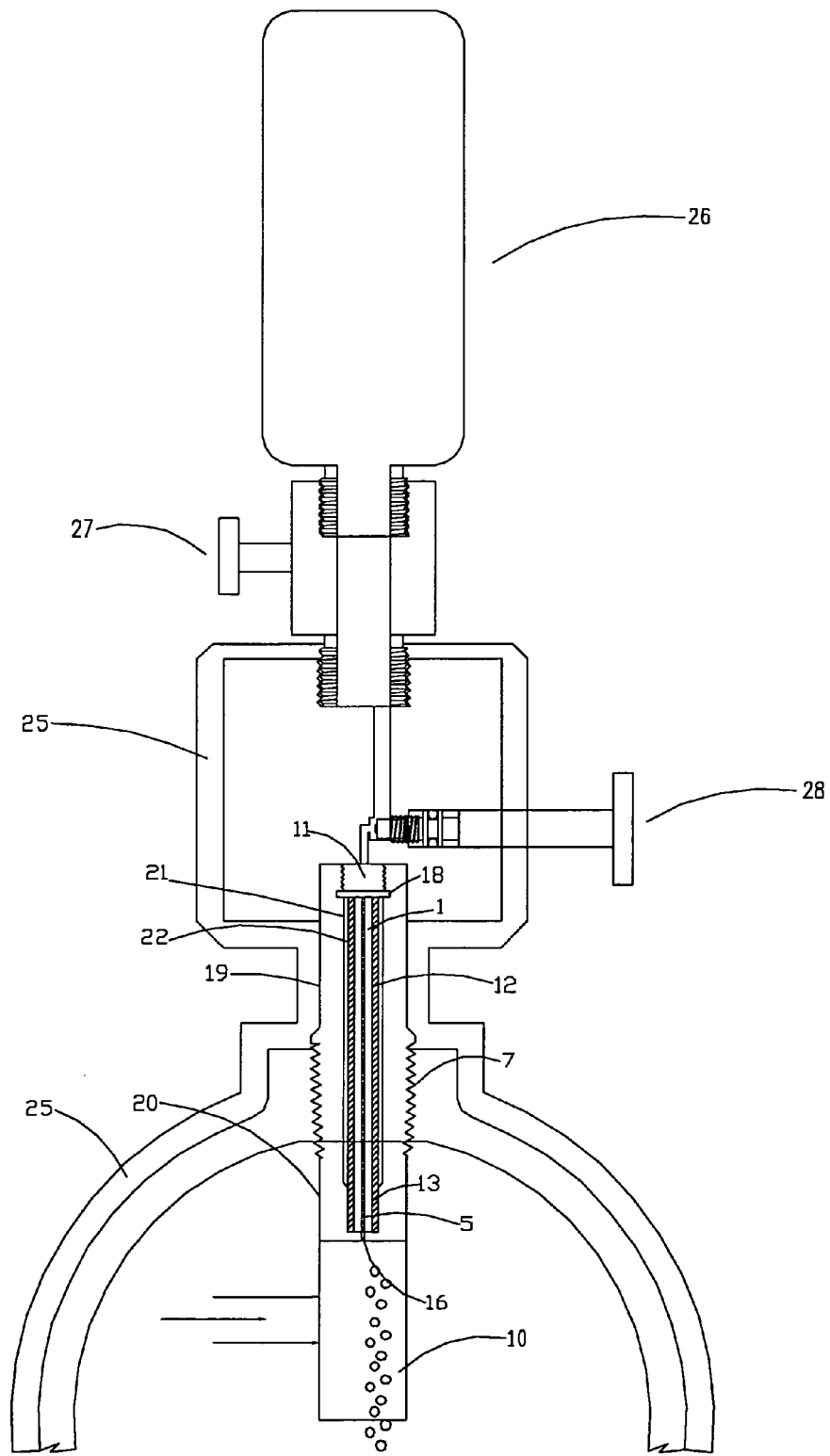
Figure #6

Figure #7
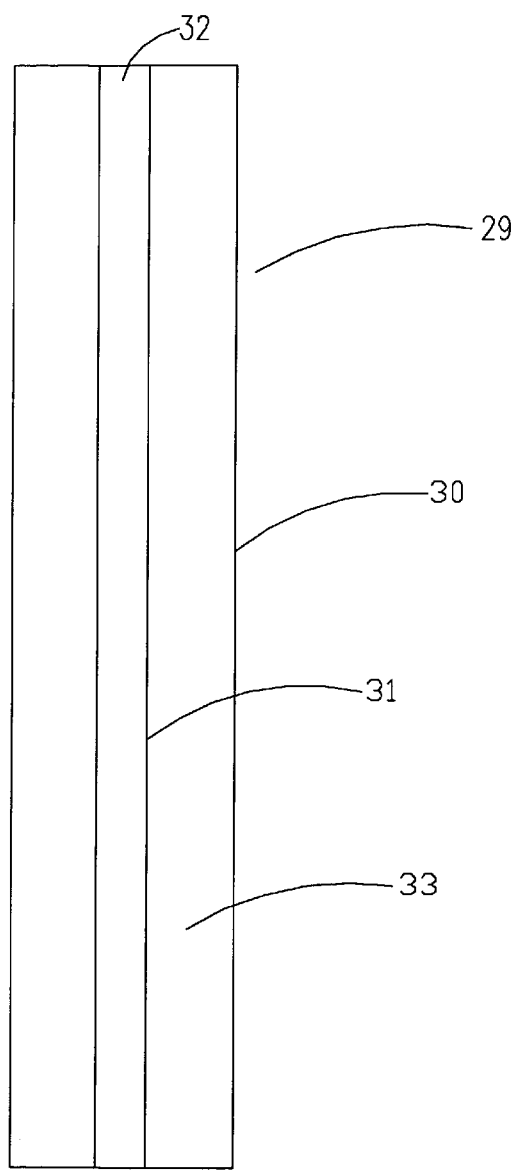
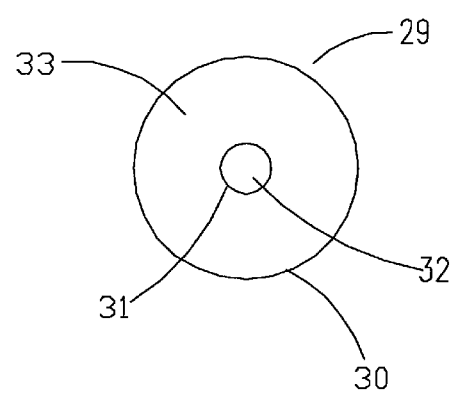

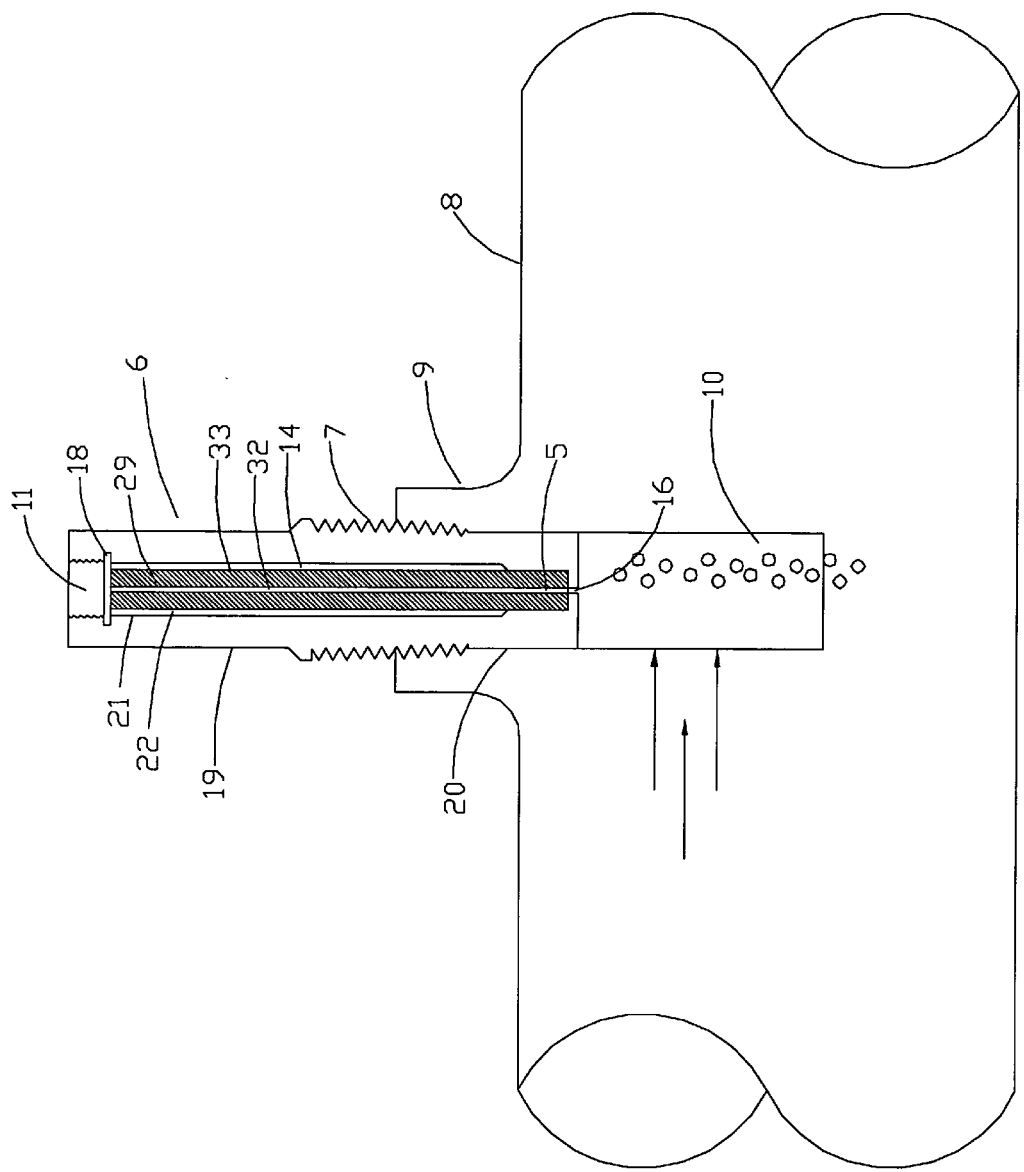

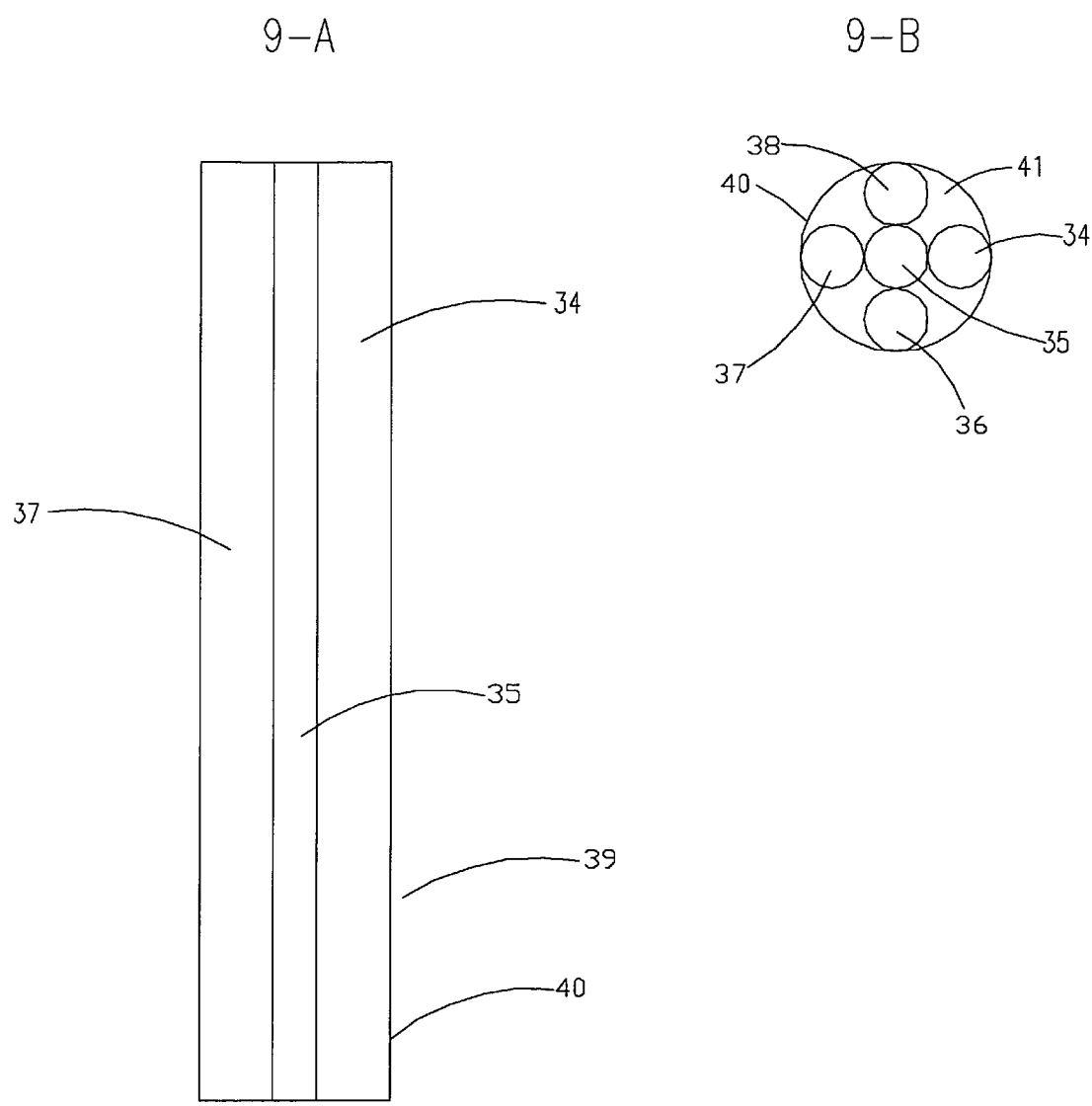
Figure #9

HEAT PIPE SAMPLE FLUID PROBE

This application is a continuation in part of U.S. patent application Ser. No. 09/915,192, filed Jul. 25, 2001, and which issued as U.S. Pat. No. 6,701,794, which claims the benefit of provisional application No. 60/221,335, filed Jul. 26, 2000, which U.S. Pat. No. 6,701,794 is also a continuation-in-part of U.S. patent application No. 09/162,239, now U.S. Pat. No. 6,357,304, having a filing date of Sep. 28, 1998, which is a continuation in part of U.S. patent application Ser. No. 08/701,406, now U.S. Pat. No. 5,841,036, filed Aug. 22, 1996.

The present application is also a continuation in part of U.S. patent application Ser. No. 10/408,026, filed Apr. 3, 2003 and issued as U.S. Pat. No. 6,904,816, which is a divisional of patent application No. 09/915,162 filed on Jul. 25, 2001, now U.S. Pat. No. 6,701,794, which U.S. Pat. No. 6,701,794 claims the benefit of provisional application No. 60/221,335, filed Jul. 26, 2000, which U.S. Pat. No. 6,701,794 is also a continuation-in-part of U.S. patent application No. 09/162,239 now U.S. Pat. No. 6,357,304 having a filing date of Sep. 28, 1998, which is a continuation in part of U.S. patent application Ser. No. 08/701,406 now U.S. Pat. No. 5,841,036, filed Aug. 22, 1996.

TECHNICAL FIELD OF THE INVENTION

The present invention relates to the sampling of process fluids such as implemented by petrochemical plants, refineries, gas separation plants, natural gas pipelines, etc., and in particular to the collection and initial conditioning of sample gas for "on-line" analyzers or filling of gas sample cylinders.

The preferred embodiment of the present invention contemplates a system configured to obtain a representative gas phase sample from a process gas containing entrained liquid, or a process gas which generally is susceptible to partial condensation of some gas phase components.

The preferred apparatus of the present invention teaches a sample probe assembly including a heat pipe configured for maintaining sample gas drawn through said sample probe at or near the source gas temperature and pressure. Accuracy of the analysis of source gas stream is enhanced and compositional changes of the gas phase are avoided by preventing the partial condensation of gas components or vaporization of entrained liquid.

BACKGROUND OF THE INVENTION

The heating value of natural gas has a significant impact on its monetary value. In general, the heating value of natural gas increases as the concentration of high molecular weight components increase. Condensation of gas phase components, which reduce the proportion of high molecular weight components, therefore tends to decrease the gas phase heating value, while vaporization of entrained liquid has the opposite effect.

It is believed that the prior art has failed to contemplate a sample probe assembly including means for maintaining sample gas drawn through said sample probe at or near the source gas temperature and pressure, to prevent condensation of gas components, or vaporization of entrained liquid, thereby increasing the accuracy of the analysis of the gas source stream.

GENERAL SUMMARY DISCUSSION OF THE INVENTION

Unlike the prior art, the present, searched for invention provides a system for retrieving a representative sample from a gas stream so that it may be either analyzed or stored in an "as is" condition, or conditioned external to the gas source by removal of entrained liquid. While heating of the sample conditioning system, including the sample probe inserted into the source gas, is beneficial to "prevent" condensation, this practice will change the gas phase composition if liquid is already present in the sample gas. For this reason, it is necessary, when liquid is present, to retain the sample gas at the original source temperature and not allow it to either cool or become heated while it is transported from the source to an analytical object such as a sample cylinder or analyzer.

The preferred embodiment of the present invention contemplates the transportation of a sample gas stream at the source gas temperature by utilization of one or more heat pipes integrated into a sample probe.

A second embodiment of the present invention preserves the sample gas at the source gas temperature by use of a vacuum jacket integrated into a sample probe.

A third embodiment of the present invention preserves the sample gas at the source gas temperature by use of an insulated passage within a sample probe.

The current practice of heat tracing sampling hardware or housing all sampling components in a heated enclosure is expensive and useful only when the source gas does not contain entrained liquid. When entrained liquid is present, heating the sample will alter the gas phase composition. (Refer to a technical paper presented by Donald P. Mayeaux at the International School of Hydrocarbon Measurement in May 2002.)

Therefore an object of the present invention is to provide means for extracting a representative sample of a source gas and to preserve its integrity as it is transported through a probe. Sample integrity is preserved by maintaining the sample gas at or near the source gas pressure and temperature. This is especially important if liquid is present in the sample gas drawn into the probe. Allowing either the sample gas pressure or temperature to change when liquid is present would almost certainly change the sample's gas phase composition.

The sample pressure in the probe is maintained at or near the source gas pressure by providing an unrestricted flow path through the probe. The flow path is of sufficient diameter to deliver sample gas at the maximum desired flow rate without appreciable pressure drop.

The sample temperature in the probe is maintained at or near the source gas temperature by integrating one or more heat pipes into the probe. The heat pipe(s) are heat sinked to the process gas and provide the heating or cooling of the sample gas necessary to maintain the sample gas at or near to the source gas temperature. An alternate method of maintaining the sample gas temperature at the source gas temperature is by utilization of a vacuum jacket. A third method is to provide an insulated passage for sample fluid within the sample probe.

A typical sample probe extends from a point inside of a pressurized gas source such as a pipeline to an external point. The external atmospheric temperature may be warmer or cooler than the source gas temperature. A heat pipe is well suited for maintaining the probe near an isothermal condition.

If liquid removal from the sample gas prior to transport through the probe is desired, this can be accomplished by use of a phase separation membrane such as that contemplated in applicant's Mayeaux U.S. Pat. No. 6,357,304 B1, incorporated herein by reference.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 1a is a side cross-sectional view of a heat pipe assembly.

FIG. 1b is a top view of a heat pipe assembly.

FIG. 2 is a side cross-sectional view of a sample probe.

FIG. 3 is a side cross-sectional view of a sample probe assembly shown installed in a pipeline.

FIG. 4 is a side cross-sectional view of a sample probe assembly with phase separation membrane shown installed in a pipeline.

FIG. 5 is a side cross-sectional view of a sample probe assembly installed in a pipeline, the exterior segment of the sample probe assembly and the exterior pipeline wall immediately surrounding the sample probe assembly are covered with insulation material.

FIG. 6 is a side cross-sectional view of a sample probe assembly installed in a pipeline and connected to a sample collection cylinder.

FIG. 7a is a cross-sectional side view of a vacuum jacket having a central passageway.

FIG. 7b is a cross-sectional top view of a vacuum jacket having a central passageway.

FIG. 8 is a side cross-sectional side view of a pipeline mounted sample probe assembly utilizing a vacuum jacketed probe.

FIG. 9a is a side cross-sectional view of a heat pipe assembly having multiple heat pipes within a housing. The sample passage consists of the area internal to the housing and external to the heat pipes.

FIG. 9b is a top view of a heat pipe assembly having multiple heat pipes within a housing. The sample passage consists of the area internal to the housing and external to the heat pipes.

DETAILED DISCUSSION OF THE INVENTION

Heat pipes are well known having been developed at the Department of Energy's Los Alamos National Laboratory more than 40 years ago. It typically consists of a metal tube (FIGS. 1a and 1b) having a small amount of working fluid 23. The working fluid's vapor 24 occupies all of the tube's inner volume not occupied by the fluid. A small amount of fluid vaporizes at the "hot end" of the tube and some of the vapor condenses at the "cold end" of the tube. The condensate returns to the tubes "hot end" through a capillary wick 4. There are many variations of heat pipe construction, which all employ the aforementioned principle of operation. By vaporization of the working fluid 23 and condensation of its vapor 24, the heat pipe strives to maintain an isothermal condition along its length.

Vacuum jackets (envelopes) are also well known. They typically consist of an outer wall 30 (FIG. 7) inner wall 31 and cavity 33 whereby said cavity 33 is evacuated. This results in a significant reduction in the ability for heat to transfer across evacuated cavity 33. Vacuum jackets are in common use in households and industry.

Referring to FIGS. 1a, 1b, 2, and 3, the preferred embodiment of the invention contemplates a sample probe utilizing a heat pipe as seen assembled in FIG. 3. Gas from a pressurized source such as pipeline 8 flows through passage 16 formed in the lower end of the probe cavity 14 (alternatively the "main" cavity), enters heat pipe central passage 5 or conduit at is lower end, flows upward and exits sample probe assembly 6, from probe outlet port 11.

The upper end 12 of probe cavity 14 is slightly larger in diameter then the lower end 13 of probe cavity 14 (refer to FIG. 2). When heat pipe assembly 1 (refer to FIGS. 1a and 1b) is inserted into probe cavity 14, as shown in FIGS. 2 and 3, the lower end L or segment of heat pipe assembly 1 is press fitted into lower end 13 of probe cavity 14. There exists a small gap 22, between probe cavity wall 21 and heat pipe outer wall 2 at the upper end 12 of probe cavity 14. The press fitted end of heat pipe assembly 1 is in the general area of probe segment 20, which is positioned inside of the gas source container or pipeline. The press fit provides good heat transfer from sample probe 15 to the lower end of heat pipe assembly 1. Conversely, gap 22 will decouple or retard heat transfer between the upper end of heat pipe assembly 1 and sample probe 15. Gap 22 is located in the general area of external probe segment 19.

In operation, heat pipe assembly 1 will transfer isothermal energy or heat into or away from the source gas S in pipeline 8 to compensate for heat transferred into or away from the heat pipe assembly by the influence of the external ambient atmosphere. For example, when the source gas is warmer than the external ambient atmosphere, heat will tend to transfer from the upper end U or segment of heat pipe assembly 1 to the upper external probe segment 19, which is located outside of the source gas. This will result in condensation of a small amount of working fluid vapor 24 in the upper end of the heat pipe assembly 1. The internal pressure of the heat pipe will tend to lower due to the loss of vapor, which in turn triggers the vaporization of enough working fluid 23 in the lower end of the heat pipe assembly 1 to replace the vapor loss from condensation, which in turn restores the heat pipe assembly's 1 internal pressure and temperature to their former levels.

The liquid, which was condensed, is transported to the lower end of heat pipe assembly 1 by capillary action of the internal wick 4. The net result is that heat loss from external probe segment 19 was restored by the heat pipe assembly's transfer of heat from the source gas surrounding internal probe segment 20. The sample probe assembly 6 temperature therefore remains essentially constant and generally equivalent with the isothermal condition of the source gas (alternatively the "fluid stream").

When the external ambient atmosphere is warmer than the source gas, the same process occurs inside of the heat pipe assembly 1. The only difference being that working fluid 23 is vaporized in the upper end of heat pipe assembly 1 and condensation of working fluid vapor 24 takes place in the lower end of heat pipe assembly 1. Heat from the external ambient atmosphere transferred to external probe segment 19 is transferred to the source gas by internal probe segment 20. This results in heat pipe assembly 1 maintaining its temperature at the approximate same temperature of the source gas.

It can be seen that various methods can be utilized to minimize heat transfer between the external ambient atmosphere and external probe segment 19. As shown in FIG. 5, one such method is the use of insulation 25 around external probe segment 19 and pipeline 8. The use of insulation 25 in this manner and gap 22 to reduce heat transfer reduces the heat load of heat pipe assembly 1 allowing it to maintain a near isothermal condition along its entire length.

Heat pipe central passage 5 is utilized for transporting gas sample within sample probe assembly 6. It is surrounded by the heat pipe within heat pipe assembly 1. Therefore gas flowing within central passage 5 is maintained at the source gas temperatures along the entire length of the sample probe assembly 6.

A second embodiment of the present invention contemplates a sample probe utilizing a vacuum jacket (refer to FIGS. 7a and 7b). As shown in FIGS. 2, 7a, 7b and 8, vacuum jacket 29 having upper and lower ends or sections is installed into probe cavity 14 of sample probe 15. Its function is to minimize or eliminate the transfer of heat between passageway 32 and external probe segment 19, maintaining the isothermal condition to generally that of the fluid stream.

As can be seen in FIGS. 7a and 7b, vacuum jacket 29 consists of inner wall 31, outer wall 30, passage 32, and cavity 33. Inner wall 31 and outer wall 30 are sealed at both ends thereby forming a closed cavity 33. Cavity 33 is evacuated to provide the required insulation effect. When a vacuum jacket 29 is employed, gas flowing through passageway 32 of said vacuum jacket 29 is maintained at essentially the source gas temperature by the aforementioned insulating action of said vacuum jacket 29.

A phase separation membrane may be utilized in cases where it is desired to remove liquid entrained in the source gas before its entry into passage 16. In such cases, a phase separation membrane 10 is integrated into the lower end of the sample probe as seen in FIGS. 4 and 8. An exemplary phase separation membrane which can be used in this application is taught in applicant's Mayeaux U.S. Pat. No. 6,357,304 B1, the contents of which are incorporated herein by reference.

In such use, sample gas flows through phase separation membrane 10 (reference FIG. 4), wherein liquid in any form is rejected by said phase separation membrane 10 and returns by gravity to the source gas, sample gas then flows through passage 16 into heat pipe central passage 5 and exits sample probe assembly 6 from probe outlet port 11. Thereafter the sample may be directed to external analytical devices such as sample cylinder 26 shown in FIG. 6.

During its passage through central passage 5 of heat pipe assembly 1, the sample is maintained at essentially the source gas temperature by the aforementioned heat transferring action of said heat pipe assembly 1. In a similar manner phase separation membrane 10 may be utilized with a vacuum jacketed probe to eliminate entrained liquid (FIG. 8).

The diameters of central passage 5 of heat pipe assembly 1 and passageway 32 of vacuum jacket 29 is sufficiently large to prevent any appreciable pressure drop at normal sample gas flow rates. It is desirable in general to prevent the pressure drop of sample gas flowing through central passageway 5 and passageway 32 from being excessive. The actual sample gas composition and intended use of said sample gas determines the maximum permissible pressure drop for a specific application.

It is possible to construct a sample probe assembly 6 having a variety of heat pipe assembly 1 configurations without detracting from the spirit of the present invention. Such an example of a variation can be seen in FIGS. 9a and 9b wherein a plurality of longitudinally aligned, self contained heat pipes (heat pipes 34, 35, 36, 37, and 38) are positioned into housing 40. The space within housing 40 not occupied by heat pipes 34, 35 36, 37, and 38 forms passage 41 to accommodate the passage of sample gas from one end to the other of heat pipe assembly 39. Heat pipe assembly 39 provides the same heat transfer service as the aforementioned heat pipe assembly 1.

An exemplary method of obtaining a sample fluid from a fluid stream utilizing the heat pipe embodiment of the present invention may comprise, for example, the steps of:
 a. providing an apparatus, comprising:
  a heat pipe having first and second segments, a length, and a main cavity formed along its length;
  a conduit having a central passage formed longitudinally therethrough, said conduit formed of thermally conductive material, said conduit situated in communication with said heat pipe;
  said first segment of said heat pipe engaging said fluid stream, so as to thermally effect said main cavity of said heat pipe;
 b. positioning said heat pipe to thermally engage said fluid stream such that said heat pipe develops an isothermal condition equivalent to said fluid stream;
 c. allowing said thermally conductive material of said conduit to thermally engage said heat pipe such that said conduit develops an isothermal condition equivalent to said heat pipe;
 d. directing a flow of sample fluid from said fluid stream into said conduit; and
 e. retrieving said sample fluid from said conduit Another example of a variation is that a heat pipe or vacuum jacket is formed integral to the fluid sample probe, as opposed to an independent heat pipe or vacuum jacket assembly being inserted into a cavity internal to said fluid sample probe.

Heat pipe assembly 1, heat pipe assembly 39 and variations of said heat pipe assemblies may be constructed to provide an essentially isothermal passage for sample gas transport.

Utilizing the source gas to stabilize the sample gas temperature, without the requirement for external heating or cooling, is of great economic and functional benefit. Any other means then heretofore described for preserving the sample gas temperature during its passage to a point external to the source gas would be of benefit. Although less effective, an insulated sample passage thru the probe may be utilized for that purpose.

| Elements of the Invention |
|---|
| U. upper end heat pipe |
| L. lower end heat pipe |
| 1. heat pipe assembly |
| 2. outer wall |
| 3. inner wall |
| 4. wick |
| 5. central passage |
| 6. sample probe assembly |
| 7. NPT threads |
| 8. pipeline |
| 9. thread "o" let |
| 10. phase separation membrane |
| 11. probe outlet port |
| 12. upper end |
| 13. lower end |
| 14. probe cavity |
| 15. sample probe |
| 16. passageway |
| 17. groove for retaining clip |

-continued

Elements of the Invention 18. retaining clip
19. external probe segment
20. internal probe segment
21. probe cavity wall
22. gap
23. working fluid
24. working fluid vapor
25. insulation
26. sample cylinder
27. sample cylinder valve
28. probe valve
29. vacuum jacket
30. outer wall
31. inner wall
32. passageway
33. cavity
34. heat pipe
35. heat pipe
36. heat pipe
37. heat pipe
38. heat pipe
39. heat pipe assembly
40. housing passage The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. An apparatus for obtaining a representative sample from a fluid stream having an isothermal condition, comprising:
a heat pipe having first and second segments, a length, and a main cavity formed along its length;
a conduit having a central passage formed longitudinally therethrough, said conduit formed of thermally conductive material, said conduit situated in communication with said heat pipe;
said first segment of said heat pipe engaging said fluid stream, so as to thermally effect said main cavity of said heat pipe;
whereby sample fluid passing through said conduit from said fluid stream maintains an isothermal condition as it passes through said central passage of said conduit.

2. The system assembly of claim 1, wherein there is further provided a plurality of heat pipes in longitudinal alignment.

3. The system assembly of claim 1, wherein said conduit is integrated within said main cavity of said heat pipe.

4. The system of claim 3, wherein said conduit is surrounded by working fluid and vapor within said main cavity of said heat pipe.

5. The system of claim 1, wherein said heat pipe is integrated into a sample probe structure.

6. The system of claim 5, wherein the sample probe has an external portion, said first segment of said heat pipe is in thermal sink with said fluid stream, and said second segment of said heat pipe thermally interfaces with said external portion of said sample probe, to offset ambient environmental temperature influence on the external portion of the fluid sample probe.

7. The system of claim 6, wherein there is further provided a phase separation membrane formed to remove liquid from a sample gas before entering said conduit.

8. The system of claim 7, wherein said sample probe has first and second ends, and wherein said first end of said fluid sample probe is positioned internal to the fluid stream and a second end is positioned external to said fluid stream.

9. The fluid sample probe of claim 6, wherein the heat pipe is formed within said sample probe structure.

10. The apparatus of claim 1, wherein said sample fluid passing through said conduit is isothermally regulated by a heat pipe so as to maintain said sample fluid at said isothermal condition of said fluid stream.

11. The method of obtaining a sample fluid having an isothermal condition from a fluid stream, comprising the steps of:
a. providing an apparatus, comprising:
a heat pipe having first and second segments, a length, and a main cavity formed along its length;
a conduit having a central passage formed longitudinally therethrough, said conduit formed of thermally conductive material, said conduit situated in communication with said heat pipe;
said first segment of said heat pipe engaging said fluid stream, so as to thermally effect said main cavity of said heat pipe;
b. positioning said heat pipe to thermally engage said fluid stream such that said heat pipe develops an isothermal condition equivalent to said fluid stream;
c. allowing said thermally conductive material of said conduit to thermally engage said heat pipe such that said conduit develops an isothermal condition equivalent to said heat pipe;
d. directing a flow of sample fluid from said fluid stream into said conduit; and
e. retrieving said sample fluid from said conduit.

12. An apparatus for obtaining a representative sample from a fluid stream having an isothermal condition, comprising:
a conduit having a central passage formed longitudinally therethrough, said conduit formed of thermally conductive material, said conduit having a portion situated exterior said fluid stream,
isothermal regulation means for maintaining said portion of said conduit exterior said fluid stream at an isothermal condition utilizing said isothermal condition of said fluid stream;
whereby sample fluid passing through said conduit from said fluid stream maintains an isothermal condition as it passes through said central passage of said conduit.

13. The apparatus of claim 12, wherein said isothermal regulation means comprises a heat pipe.

14. The method of obtaining a sample fluid having an isothermal condition from a fluid stream, comprising the steps of:
a. providing an apparatus, comprising:
a conduit having a central passage formed longitudinally therethrough and a length, said conduit formed of thermally conductive material, said conduit having a portion situated exterior said fluid stream,
temperature regulation means for maintaining said conduit at said isothermal condition of said fluid stream;
b. allowing said thermally conductive material of said conduit to thermally engage said fluid stream such that said conduit develops an isothermal condition equivalent to said fluid stream;
c. directing a flow of sample fluid from said fluid stream into said conduit while allowing said temperature regulation means to thermally isolate said conduit from ambient temperature along said length of said conduit; and
d. retrieving said sample fluid from said conduit.

* * * * *